United States Patent
Sakai

(10) Patent No.: US 7,813,795 B2
(45) Date of Patent: Oct. 12, 2010

(54) ABDOMINAL IMPEDANCE MEASUREMENT APPARATUS AND BODY COMPOSITION DETERMINATION APPARATUS

(75) Inventor: Yoshio Sakai, Shiki (JP)

(73) Assignee: Tanita Corporation, Tokyo (JP)

( * ) Notice: Subject to any disclaimer, the term of this patent is extended or adjusted under 35 U.S.C. 154(b) by 49 days.

(21) Appl. No.: 12/073,552

(22) Filed: Mar. 6, 2008

(65) Prior Publication Data

US 2008/0221476 A1   Sep. 11, 2008

(30) Foreign Application Priority Data

Mar. 6, 2007   (JP) ............................ 2007-055204

(51) Int. Cl.
A61B 5/05   (2006.01)
(52) U.S. Cl. ..................................... 600/547
(58) Field of Classification Search ................. 600/547, 600/390
See application file for complete search history.

(56) References Cited

U.S. PATENT DOCUMENTS

| 5,657,369 | A | 8/1997 | Stein et al. ................... 378/208 |
| 7,283,869 | B2 * | 10/2007 | Onda et al. ................... 600/547 |
| 7,594,896 | B2 * | 9/2009 | Sakai et al. ................... 600/587 |
| 2004/0077969 | A1 * | 4/2004 | Onda et al. ................... 600/547 |
| 2005/0222516 | A1 | 10/2005 | Kasahara et al. ............. 600/547 |
| 2007/0038140 | A1 * | 2/2007 | Masuo et al. ................. 600/547 |
| 2008/0021349 | A1 | 1/2008 | Sakai et al. ................... 600/587 |
| 2008/0243026 | A1 * | 10/2008 | Tsuji ........................... 600/547 |
| 2009/0024053 | A1 * | 1/2009 | Kasahara ..................... 600/547 |
| 2009/0182243 | A1 * | 7/2009 | Oku et al. .................... 600/547 |
| 2009/0247896 | A1 * | 10/2009 | Kanai et al. ................. 600/547 |

FOREIGN PATENT DOCUMENTS

| EP | 1 882 448 A1 | 1/2008 |
| JP | 11-113870 | 4/1999 |
| JP | 2005-288023 | 10/2005 |
| WO | WO 02/065900 | 8/2002 |

OTHER PUBLICATIONS

Hermann Scharfetter et al., "Assessing Abdominal Fatness with Local Bioimpedance Analysis: Basics and Experimental Findings," [online], [Found in a search performed on Feb. 15, 2007], Internet URL: http://www.imt.tugraz.at/scharfetter/no_sync/publications/scharfetter_IJO_01.pdf#search='hermann%20scharfetter%20assessing%20abdominal.
European Search Report dated Jun. 12, 2008 corresponding to EP 08 00 4030.

* cited by examiner

*Primary Examiner*—Max Hindenburg
*Assistant Examiner*—H. Q. Nguyen
(74) *Attorney, Agent, or Firm*—Hogan Lovells US LLP

(57) ABSTRACT

An abdominal impedance measurement apparatus includes a plurality of electrodes for measuring an abdominal impedance of a human subject, electrode supporting member for supporting the electrodes, and a frame that is disposable around the human subject. A light emitter is supported by the frame for emitting light beams toward the inside of the frame. A mark is provided at the electrode supporting member. This mark is capable of being irradiated with the light beams.

10 Claims, 7 Drawing Sheets

ABDOMINAL IMPEDANCE MEASUREMENT APPARATUS AND BODY COMPOSITION DETERMINATION APPARATUS

BACKGROUND OF THE INVENTION

1. Field of the Invention

The present invention relates to abdominal impedance measurement apparatuses and body composition determination apparatuses for human bodies.

2. Description of Prior Art

For correctly taking measurements of areas of visceral fat and subcutaneous fat in the bodies of humans, body fat determination apparatuses have been used which calculates body fat data on the basis of tomographic images obtained by various CT (computed tomography) procedures, including X-ray CT and impedance CT, or by MRI (magnetic resonance imaging).

Conventionally, studies have been made in which indexes of body fat were calculated on the basis of impedances measured using impedance measuring electrodes that may be brought into contact with the abdomen of a human subject. For example, according to one study, the mass or area of visceral fat of a human body is calculated on the basis of an impedance measured using a pair of current-supplying electrodes in contact with the anterior and posterior surfaces of the abdomen and voltage-measurement electrodes in contact with flanks of the abdomen, and by the waist circumference. The calculation method is obtained by correlation among the results of CT, the impedance, and the waist circumference, as disclosed in Miwa RYO, Development of Visceral-fat Measuring Method Using Abdominal Bioelectrical Impedance, Himan Kenkyu (Journal of Japan Society for the Study of Obesity), Japan, Japan Society for the Study of Obesity, 2003, Vol. 9, No. 2, pp. 32-38.

There has also been a study in which impedance measurement electrodes are mounted on a belt that is wound around the abdomen of a human subject, whereby the impedance measurement electrodes are brought into contact with the anterior surface of the abdomen, and the subcutaneous fat mass is estimated from the measured abdominal impedance, as disclosed in Hermann SCHARFETTER and five others, Assessing abdominal fatness with local bioimpedance analysis: Basics and experimental findings), [online], [Found in a search performed on Feb. 15, 2007], Internet URL: http://www.imt.tugraz.at/scharfetter/no_sync/publications/scharfetter_IJO_01.pdf#search='hermann%20scharfetter%20assessing%20abdominal' and in JP-A-11-113870.

In the measurement of bioimpedance in humans, even for the same human subject, the measured results may vary depending on the positions of the measurement electrodes. Therefore, in order to ensure the reproducibility of measurements, the measurement electrodes should always be placed at the same locations. For example, it is possible to consider the transverse plane that passes through the navel of a human subject and is vertical to the median line to be the reference plane relative to which measurement electrodes should always be arranged.

However, it is difficult, in practice, to arrange impedance measurement electrodes at such reference positions. For example, in the method in which a belt on which impedance measurement electrodes are arranged is wound around the abdomen, there is the possibility that the positions of the measurement electrodes may be out of alignment by deformation of the belt. Furthermore, when the belt is wound around the abdomen, the reference positions cannot be definitely confirmed in most instances because the reference positions cannot be seen by the human subject or by anyone else due to the belt.

SUMMARY OF THE INVENTION

Accordingly, the present invention provides an abdominal impedance measurement apparatus that enables the impedance measurement electrodes to be arranged at reference positions accurately, and a body composition determination apparatus including the abdominal impedance measurement apparatus.

In accordance with an aspect of the present invention, an abdominal impedance measurement apparatus includes: a plurality of electrodes for measuring an abdominal impedance of a human subject; an electrode supporting member for supporting the electrodes; a frame that is disposable around the human subject; a light emitter supported by the frame for emitting a light beam toward the inside of the frame; and a mark provided at the electrode supporting member, the mark being capable of being irradiated with the light beam. For using the abdominal impedance measurement apparatus, with the assistance of the light beam emitted from the light emitter on the human subject, the frame can be adjusted to an appropriate position and an appropriate orientation with respect to reference positions for measurement. Afterward, the position and orientation of the electrode supporting member can be adjusted so that the position of the light beam coincides with the mark on the electrode supporting member. Thus, the electrodes can be arranged on the reference positions for measurement accurately, so that bioimpedance can be measured with a high level of reproducibility.

In a preferred embodiment, the electrodes are aligned along a longitudinal direction of the electrode supporting member. The light emitter emits light beams onto at least two points. The above-mentioned mark includes a part extending along the longitudinal direction of the electrode supporting member. The position and orientation of the electrode supporting member will be adjusted so that the two points of the light beams coincide with the part of the mark extending along the longitudinal direction of the electrode supporting member. As a result, the electrodes that are aligned along the longitudinal direction of the electrode supporting member can be arranged in a desirable direction.

In another preferred embodiment, the electrodes are aligned along a longitudinal direction of the electrode supporting member. The light emitter emits light beams onto at least three points. The mark is of a cross shape including a part extending along the longitudinal direction of the electrode supporting member and another part orthogonal to the part extending along the longitudinal direction. The position and orientation of the electrode supporting member will be adjusted so that the two points of the light beams coincide with the part of the mark extending along the longitudinal direction of the electrode supporting member. As a result, the electrodes that are aligned along the longitudinal direction of the electrode supporting member can be arranged in a desirable direction. Furthermore, the position and orientation of the electrode supporting member will be adjusted so that the other point of the light beam coincides with the other part of the mark orthogonal to the part extending along the longitudinal direction. As a result, the electrodes that are aligned along the longitudinal direction of the electrode supporting member can be arranged at appropriate positions in a desirable direction.

In accordance with an aspect of the present invention, an abdominal impedance measurement apparatus includes: a plurality of electrodes for measuring an abdominal impedance of a human subject; an electrode supporting member for supporting the electrodes; a frame which that is disposable around the human subject; a light emitter supported by the frame for emitting a light beam toward the inside of the frame; and a light receiving element provided at the electrode supporting member, the light receiving element being capable of being irradiated with the light beam. For using the abdominal impedance measurement apparatus, by the aid of the light beam emitted from the light emitter on the human subject, the frame can be adjusted to an appropriate position and an appropriate orientation with respect to reference positions for measurement. Afterward, the position and orientation of the electrode supporting member can be adjusted so that the position of the light beam coincides with the light receiving element on the electrode supporting member. Thus, the electrodes can be accurately arranged at the reference positions for measurement, so that bioimpedance can be measured with a high level of reproducibility.

In a preferred embodiment, the electrodes are aligned along a longitudinal direction of the electrode supporting member. The light emitter emits light beams onto at least two points. At least two light receiving elements are provided at the electrode supporting member, the light receiving elements being capable of being irradiated with the at least two points of the light beams, the light receiving elements being aligned in a line extending along the longitudinal direction of the electrode supporting member. The position and orientation of the electrode supporting member will be adjusted so that the at least two points of the light beams coincide with the light receiving elements aligned in a line extending along the longitudinal direction of the electrode supporting member. As a result, the electrodes that are aligned along the longitudinal direction of the electrode supporting member can be arranged in a desirable direction.

In another preferred embodiment, the electrodes are aligned along a longitudinal direction of the electrode supporting member. The light emitter emits light beams onto at least three points. At least three light receiving elements being provided at the electrode supporting member, the light receiving elements being capable of being irradiated with the at least three points of the light beams, two of the light receiving elements being aligned in a line extending along the longitudinal direction of the electrode supporting member. The position and orientation of the electrode supporting member can be adjusted so that at least two points of the light beams coincide with the light receiving elements aligned in a line extending along the longitudinal direction of the electrode supporting member. As a result, the electrodes that are aligned along the longitudinal direction of the electrode supporting member can be arranged in a desirable direction. Furthermore, the position and orientation of the electrode supporting member will be adjusted so that the other point of the light beam coincides with the other light receiving element. As a result, the electrodes that are aligned along the longitudinal direction of the electrode supporting member can be arranged at appropriate positions in the desirable direction.

In this specification, "emits light beams onto at least two points" does not mean emitting light rays onto a single wide area including the two points; the meaning includes at least (1) emitting light beams onto two or more separate spots, and (2) emitting light beams onto a straight line passing through two or more separate spots.

In this specification, "emits light beams onto at least three points" does not mean emitting light rays onto a single wide area including all three points; the meaning includes at least (1) emitting light beams onto three or more separate spots, (2) emitting light beams onto a straight line passing through two or more separate spots and onto another spot, and (3) emitting light beams onto two straight lines orthogonal to each other, each of the straight lines passing through two or more points.

Among the above examples, it is preferable that the light emitter emit the light beams onto a straight line and a spot. This is because a straight line irradiated by a light beam is conspicuous and suitable as a mark, whereas emitting light beams onto a plurality of straight lines leads to an increase in consumption of energy. When the cross-shaped mark is used, the position and orientation of the electrode supporting member will be suitable if the straight line irradiated by a light beam conforms to one of the two lines of the cross, and a spot irradiated by another light beam conforms to the other line of the cross. When the three light receiving elements are used, the position and orientation of the electrode supporting member will be suitable if the straight line irradiated by a light beam conforms to two light receiving elements and a spot irradiated by another light beam conforms to the other light receiving element.

A body composition determination apparatus according to the present invention includes: any one of the aforementioned abdominal impedance measurement apparatuses; distance measuring devices located at the frame, each of the distance measuring devices outputting a signal corresponding to a distance from the distance measuring device to an abdominal part of the human subject; a width estimator for estimating a width value of the abdominal part of the human subject on the basis of signals output by the distance measuring devices; and a body composition index calculator for calculating an index of a body composition of the human subject on the basis of the impedance measured by the abdominal impedance measurement apparatus and the width value estimated by the width estimator. According to the body composition determination apparatus, since the electrodes can be arranged at the reference positions so that accurate measurements can be taken, an index of a body composition can be determined with a high level of reproducibility.

DETAILED DESCRIPTION OF PREFERRED EMBODIMENTS

Figure 1:
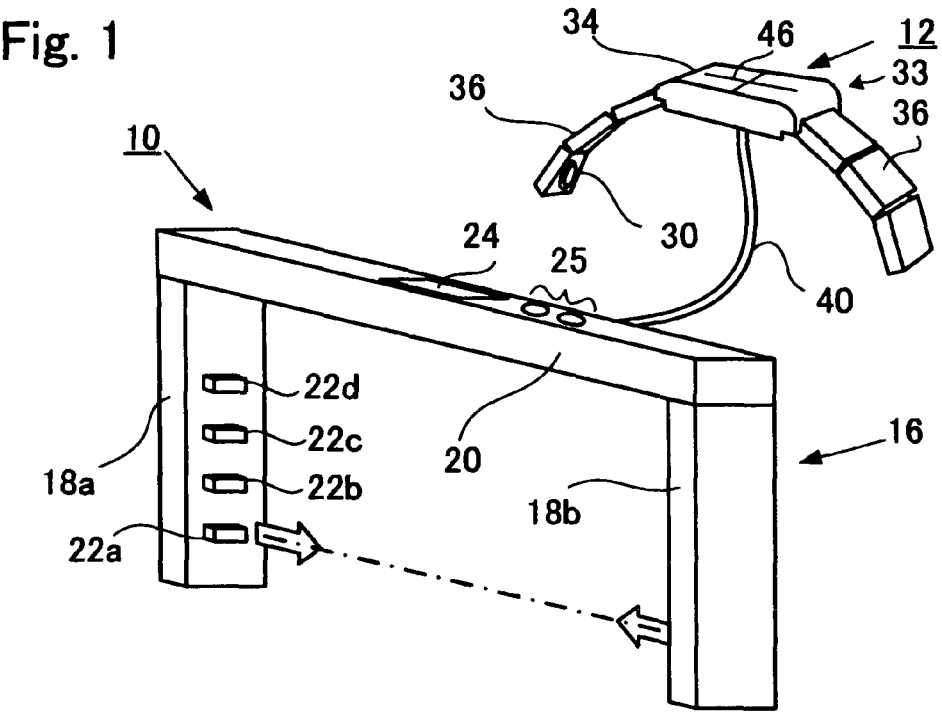
FIG. 1 is a perspective view showing a body composition determination apparatus according to a first embodiment of the present invention.

With reference to the accompanying drawings, various embodiments according to the present invention will be described hereinafter. In the drawings, scales of lengths may differ from those in the actual product.

First Embodiment

Figure 2:
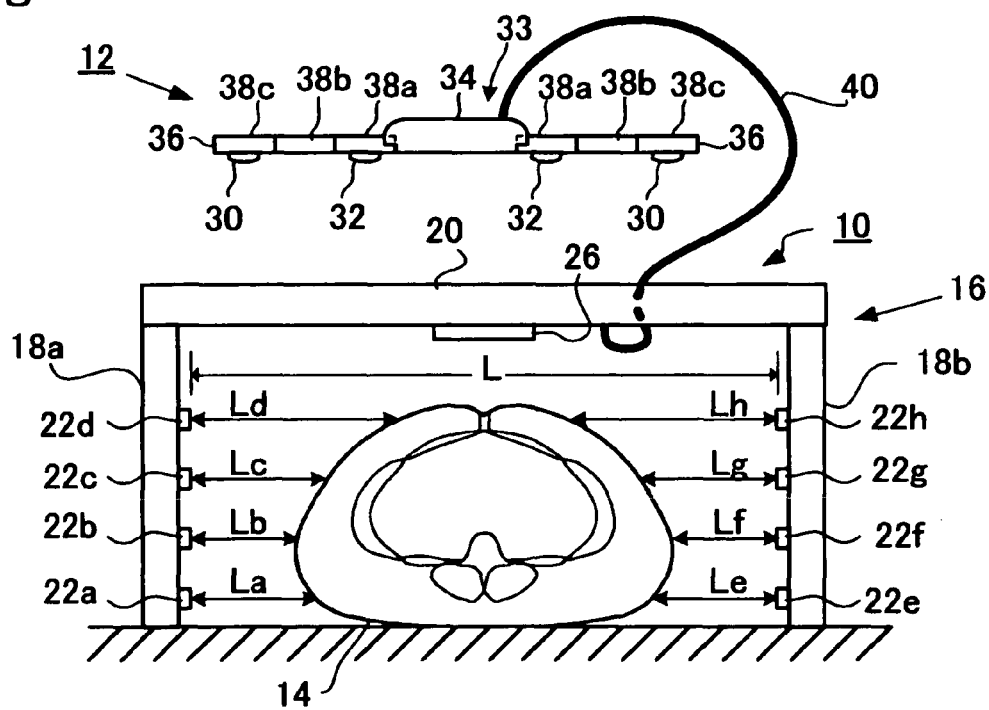
FIG. 2 is a front view showing the body composition determination apparatus in FIG. 1.

FIG. 1 is a perspective view of a body composition determination apparatus according to a first embodiment of the present invention, and FIG. 2 is a front view of the body composition determination apparatus. The body composition determination apparatus includes an abdominal width determination apparatus 10 and an impedance measuring unit 12. As will be described later, the abdominal impedance measurement apparatus according to the embodiment includes some parts of the abdominal width determination apparatus 10 and the whole of the impedance measuring unit 12.

As shown in FIG. 2, the abdominal width determination apparatus 10 includes a casing (housing), i.e., a frame 16, at the inside of which a human being, i.e., a human subject 14, may be positioned. The frame 16 is portable, and it is generally U-shaped and generally rectangular and has one side that is open, whereby the human subject easily positioned inside the frame. Therefore, even if the human subject 14 is a bedridden disabled person or an elderly bedridden person, the frame 16 can be positioned easily around the human subject 14.

The frame 16 has a pair of generally parallel legs 18a and 18b and a connection part 20 fixed on the top of each of the legs 18a and 18b. The legs 18a and 18b are placed on a floor or bed on which the human subject 14 lies supine, and the connection part 20 is opposed to the anterior surface of the abdomen of the human subject 14, with the subject lying on the subject's back.

Distance measuring devices are mounted on the frame 16 for measuring distances among a plurality of known positions and a plurality of measured points on the outline of the human subject 14. In this embodiment, the distance measuring devices include a plurality of optical distance sensors 22 mounted on the inner surfaces of the frame 16. The optical distance sensors 22 are arranged in a perpendicular plane. In the drawings, suffixes a through h are attached to reference number 22 in order to identify individual distance sensors 22. In the illustrated embodiment, eight distance sensors 22a through 22h are provided, but the number of distance sensors 22 is not limited to that in this embodiment. The sensors 22a through 22d are fixedly secured at the leg 18a, whereas the sensors 22e through 22h are fixedly secured at the leg 18b. The distance-interval between the array of the sensors 22a through 22d and the array of the sensors 22e through 22h is referred to as L.

Although it is not shown, each of the optical distance sensors 22 includes a light emitter for emitting a light beam (such as, for example, but not limited to, an infrared light beam) and a light receiving element for receiving the light reflected from a measured point on the human subject 14. On the basis of the state of the received light, the light receiving element generates an electric signal corresponding to the distance from the corresponding sensor to the measurement point.

La through Lh in FIG. 2 designate the distance measured by the sensors 22a through 22h, respectively. The light receiving element of each optical distance sensor 22 receives light reflected from a point at which the horizontal line (distance-measurement line) passing through the corresponding distance sensor 22 intersects with the human subject 14. This point is the measurement point that the distance sensor 22 measures. For example, the light receiving element of the optical distance sensors 22a receives light reflected from a point at which the horizontal line passing through the corresponding distance sensor 22a intersects with the human subject 14, and generates an electric signal corresponding to the distance La from the corresponding sensor 22a to the point. Similarly, sensors 22b through 22h generate electric signals corresponding to the distances Lb through Lh, respectively. The arrows in FIG. 1 represent directions of the distance-measurement lines of the sensors 22a and 22e. The dashed line connecting the sensors 22a and 22e indicates that the distance-measurement lines are in one straight line. The distance-measurement lines of the sensors 22b and 22f are also in a straight line. The distance-measurement lines of the sensors 22c and 22g are also in a straight line. The distance-measurement lines of the sensors 22d and 22h are also in a straight line.

A console of the body composition determination apparatus is disposed at the connection part 20. More specifically, as shown in FIG. 1, there are provided a display 24 for displaying operation guidance of the body composition determination apparatus and determination results; and a manual interface 25 including buttons, etc., for providing commands to the body composition determination apparatus in response to manipulation by the operator. Inside the connection part 20, electrical circuitry, which will be described later, is provided for controlling the body composition determination apparatus 1.

As shown in FIG. 2, a light emitter 26 is located at the connection part 20 for emitting a light beam toward the inside of the frame 16. The light emitter 26 is, for example, but is not limited to a laser that emits a light beam 60 of which the cross section is a narrow straight line and a light beam 62 of which the cross section is a small spot (see FIGS. 7 and 8). The light emitter 26 may be constituted of two light emitting elements that emit a linear light beam 60 and spot light beam 62, respectively, or may be constituted of a single light emitting element.

The light beam 60 irradiates a linear area in its radiation field. The linear area extends parallel to the longitudinal direction of the connection part 20 of the frame 16. Consequently, the linear light beam 60 is a projection of the longitudinal axis of the connection part 20. The light beam 62 is emitted from the center of the connection part 20 in the longitudinal direction toward the direction orthogonal to the connection part 20. The light beam 62 irradiates a spot area in its radiation field. Consequently, the spot light beam is a projection of the center point of the connection part 20 in the longitudinal direction. By the aid of the light beams emitted from the light emitter 26, the operator can adjust the frame 16 (and thus the sensors 22a through 22h) to an appropriate position and an appropriate orientation with respect to the human subject 14. For example, the frame 16 can be deployed in the transverse plane that passes through the navel of the human subject 14 and is vertical to the median line of the human subject 14, and thereby, the sensors 22a through 22h are deployed in the transverse plane. As will be described later, by the aid of the light beams emitted from the light emitter 26, the operator can also adjust the impedance measuring unit 12 to an appropriate position and an appropriate orientation with respect to the human subject 14.

Figure 3:
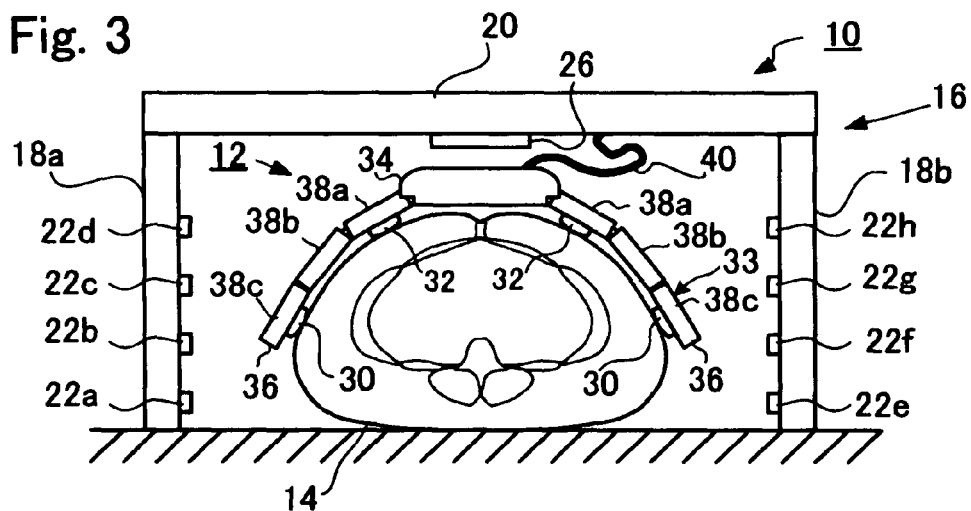
FIG. 3 is a front view showing the body composition determination apparatus in FIG. 1 which is measuring bioimpedance of a human subject.
Figure 4:
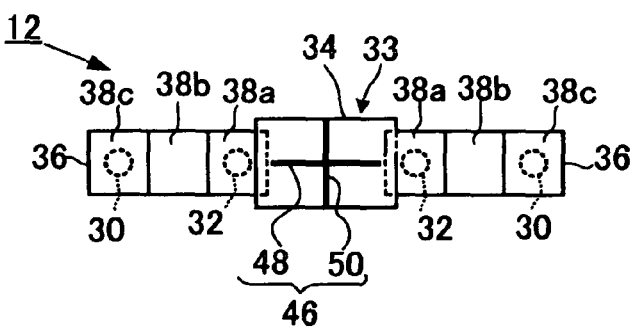
FIG. 4 is a plan view showing an impedance measuring unit in the body composition determination apparatus in FIG. 1.

As shown in FIGS. 2 through 4, the impedance measuring unit 12 includes a plurality of electrodes 30 and 32 for measuring the abdominal impedance of a human subject, and an electrode supporting member 33 for supporting the electrodes 30 and 32. The electrode supporting member 33 includes a handle 34 that the operator holds, and a pair of arms 36 extending from each end of the handle 34 in the longitudinal direction of the handle 34. In this embodiment, each arm 36 includes three segments 38a, 38b, and 38c, but the number of segments constituting each arm is not limited to that in this embodiment.

Although not shown in detail, the segment 38a is hinged to the handle 34, the segment 38b is hinged to the segment 38a, and the segment 38c is also hinged to the segment 38b. Therefore, the electrode supporting member 33 of the impedance measuring unit 12 can be bent at the edges of these elements. These segments are all of the same size, and the impedance measuring unit 12 is axisymmetric with respect to the handle 34 when both arms 36 are in mutually corresponding positions.

Current supplying electrodes 30 are attached to the lower surface of the segments 38c that are farthest from the handle 34, whereas voltage-measurement electrodes 32 are attached to the lower surface of the segments 38a that are nearest to the handle 34. The electrodes 30 and 32 are used in such a manner that they are in contact with the human subject 14 as shown in FIG. 3, that is, the current-supplying electrodes 30 apply an electrical alternate current to the human subject 14 and the voltage-measurement electrodes 32 are used for measuring the voltage between the voltage-measurement electrodes 32. The bioimpedance of the abdomen of the human subject 14 can be calculated on the basis of the current and the voltage. Since the electrode supporting member 33 of the impedance measuring unit 12 is bendable, the electrodes 30 and 32 can be appropriately in contact with the abdomen of the human subject 14. As shown in FIG. 4, the electrodes 30 and 32 are aligned in the longitudinal direction of the electrode supporting member 33.

Inside the connection part 20 of the frame 16, a current-supply circuit 42 (see FIG. 5) is provided for supplying an electrical alternate current to the current-supplying electrodes 30, and a voltage-measurement circuit 44 (see FIG. 5) is provided for measuring the voltage between the measurement electrodes 32. A cable 40 connecting the connection part 20 and the handle 34 contains wires for electrically connecting these circuits and the electrodes 30 and 32. The impedance measuring unit 12 is movable with respect to the frame 16 within a space defined by the length of the cable 40.

On the upper surface of the handle 34 of the impedance-measuring unit 12, a cross-shaped mark 46 is provided. As the mark 46, a cross pattern which is printed or which is handwritten, or which is a raised cross, may be used, but in this embodiment, a cross that is formed by grooves is used. More specifically, the mark 46 of this embodiment includes a longitudinal groove 48 extending along the longitudinal direction of the electrode supporting member 33 of the impedance measuring unit 12, and a transverse groove 50 that extends along the width direction of the electrode supporting member 33 and is orthogonal to the longitudinal groove 48. The mark 46 can be irradiated by the light beams from the light emitter 26, and as will be described later, by the aid of the light beams from the light emitter 26, the operator can adjust the impedance measuring unit 12 (and thus the current supplying electrodes 30 and 32) in an appropriate position and an appropriate orientation with respect to the human subject 14.

Figure 5:
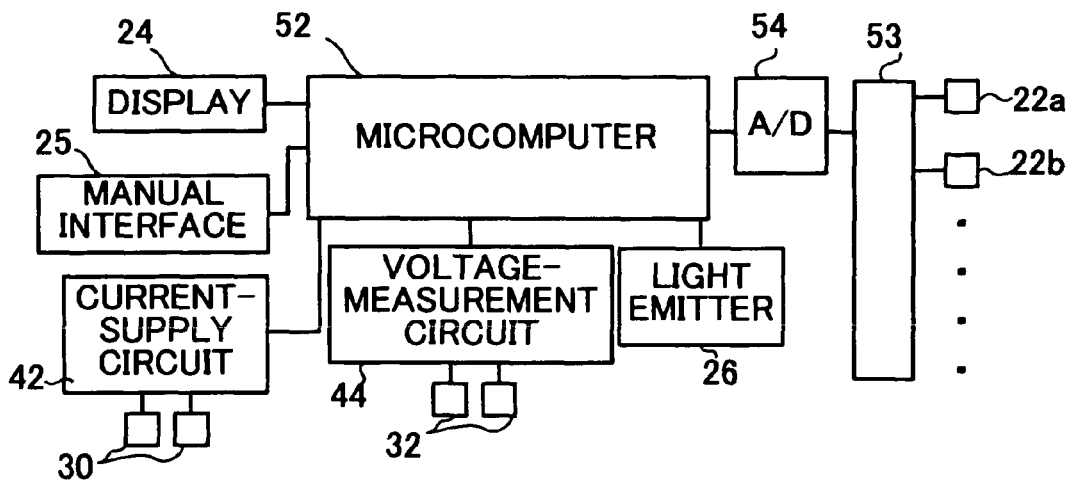
FIG. 5 is a block diagram showing an electric structure of the body composition determination apparatus in FIG. 1.

Next, with reference to FIG. 5, the electrical structure of the body composition determination apparatus will be described. Inside the connection part 20 of the frame 16, electrical circuitry is provided for controlling the body composition determination apparatus 1. More specifically, inside the connection part 20, a microcomputer 52, a switch 53, an A/D (analog-to-digital) converter 54, the aforementioned current-supply circuit 42, and the aforementioned voltage-measurement circuit 44 are provided. The microcomputer 52 is electrically connected with the display 24, the manual interface 25, the current-supply circuit 42, the voltage-measurement circuit 44, the light emitter 26, and A/D converter 54.

In response to a command from the manual interface 25, the microcomputer 52 makes the light emitter 26 emits the light beams. In response to a command to determine the abdominal width from the manual interface 25, the microcomputer 52 drives a driving mechanism for the sensors (not shown) to cause the light emitting elements of the sensors 22a through 22h to emit the light beams.

The switch 53 transfers the output signals from the light receiving elements of the optical distance sensors 22a through 22h to the A/D converter 54 one by one in sequence. The A/D converter 54 converts the signal supplied from the switch 53 into a digital signal sequentially. The digital signal is supplied to the microcomputer 52. Thus, the digital distance signals corresponding to the output signals from the optical distance sensors 22a through 22h are supplied to the microcomputer 52. Each of the digital distance signals represents the gap distance between the corresponding optical distance sensor 22 and the measured point on the human subject 14 corresponding to the corresponding optical distance sensor 22.

The microcomputer 52 serves as a width estimator for estimating the abdominal width value of the human subject 14 on the basis of the distance signals output from the sensors. For this purpose, the microcomputer 52 calculates the inter-measured-point distances of the abdomen of the human subject 14 on the basis of the distance signals. More specifically, based on the distance signals from the sensors 22a and 22, the microcomputer 52 calculates inter-measured-point distance W1 in accordance with the following equation (see FIG. 2):

$$W1 = L - La - Le$$

On the basis of the distance signals from the sensors 22b and 22f, inter-measured-point distance W2 is calculated as W2=L−Lb−Lf. Furthermore, based on the distance signals from the sensors 22c and 22g, inter-measured-point distance W3 is calculated as W3=L−Lc−Lg, whereas based on the distance signals from the sensors 22d and 22h, inter-measured-point distance W4 is calculated as W4=L−Ld−Lh.

Afterward, serving as the width estimator, the microcomputer 52 selects the maximum value from among inter-measured-point distances W1 through W4. This maximum value is considered as the abdominal width value of the human subject 14. The microcomputer 52 makes the display 24 show the width value.

Upon receiving a command to measure impedance from the manual interface 25, the microcomputer 52 drives the current-supply circuit 42 and the voltage-measurement circuit 44, so that the current-supply circuit 42 passes an electrical alternate current between the current supplying electrodes 30 and the voltage-measurement circuit 44 measures the voltage between the voltage-measurement electrodes 32. The microcomputer 52 calculates the bioimpedance on the basis of the voltage measured by the voltage-measurement circuit 44 and the current supplied to the current supplying electrodes 30.

The abdominal impedance measurement apparatus according to the embodiment includes the aforementioned impedance measuring unit 12 and some parts (specifically, the frame 16, the light emitter 26, and the microcomputer 52) of the abdominal width determination apparatus 10.

The microcomputer 52 further serves as a body composition index calculator for calculating body composition indexes on the basis of the impedance measured by the abdominal impedance measurement apparatus (i.e., calculated by the microcomputer 52) and the width value estimated by the microcomputer 52. The body composition indexes include, for example, but are not limited to, subcutaneous fat thickness, abdominal muscle thickness, subcutaneous fat area, visceral fat area, total fat area of the abdomen, fat ratio of trunk portion, and fat ratio of the entire body. The theories for determining the body composition indexes are known, e.g., in Japanese Patent Application Publication JP-2005-288023-A (published in 2005), and therefore they are not described here. The disclosure of Japanese Patent Application Publication JP-2005-288023-A is herein incorporated by reference in its entirety. The microcomputer 52 causes the display 24 to show these calculated indexes.

Figure 6:
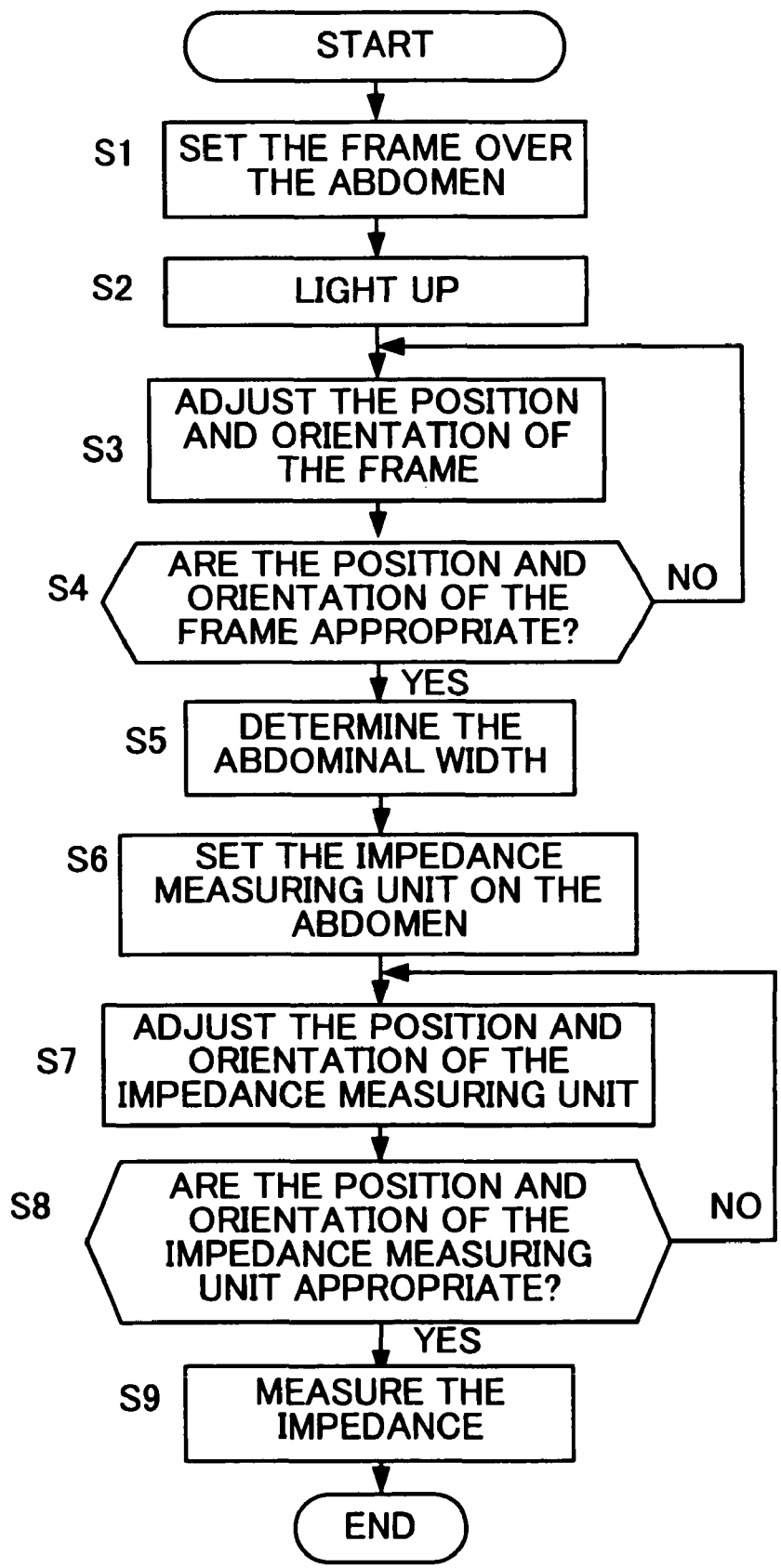
FIG. 6 is a flowchart showing the procedure of use of the body composition determination apparatus in FIG. 1.

Next, with reference to FIG. 6, a method for using the body composition determination apparatus of the embodiment will be described. FIG. 6 is a flowchart showing the procedure of use of the body composition determination apparatus. First, the operator sets the frame 16 on the floor or bed in such a manner that the frame 16 lies over the abdomen of the human subject 14 as shown in FIG. 2 (step S1).

Then, the operator manipulates the manual interface 25 to drive the light emitter 26 for irradiating light onto the abdomen of the human subject 14 (step S2). According to the manipulation by the operator, the manual interface 25 provides the microcomputer 52 with a command to drive the light emitter 26. Upon receiving the command, the microcomputer 52 causes the light emitter 26 to emit light. As described above, the light emitter 26 emits a light beam 60 of which the cross section is a narrow straight line and a light beam 62 of which the cross section is a small spot (see FIGS. 7 and 8). By the aid of the light beams emitted from the light emitter 26, the operator adjusts the frame 16 (and thus the sensors 22a through 22h) to an appropriate position and an appropriate orientation with respect to the human subject 14 (steps S3 and S4).

Figure 7:
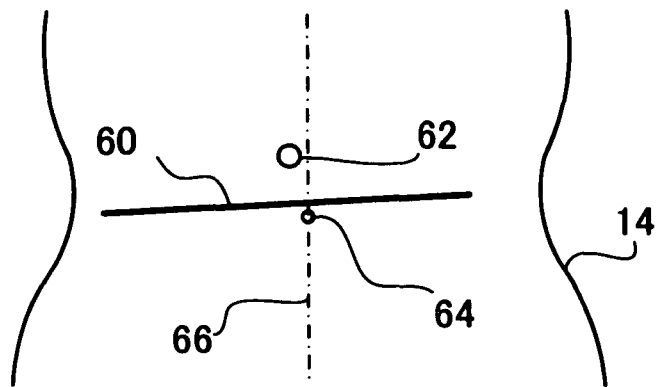
FIG. 7 is a plan view showing the abdomen of a human subject irradiated by a linear light beam and a spot light beam emitted by a light emitter in the body composition determination apparatus in FIG. 1.

The target position and orientation is such that the frame 16 is located without inclination in the transverse plane that passes through the navel 64 (see FIGS. 7 and 8) of the human subject 14 and is vertical to the median line of the human subject 14. The linear light beam 60 is a projection of the longitudinal axis of the connection part 20 of the frame 16. Thus, if the linear light beam 60 does not irradiate the navel 64 (e.g., as shown in FIG. 7), the operator can understand that the frame 16 is not located in the transverse plane that passes through the navel 64 of the human subject 14 and is vertical to the median line of the human subject 14. In this case, the operator adjusts the position of the frame 16 so that the linear light beam 60 irradiates the navel 64.

Figure 8:
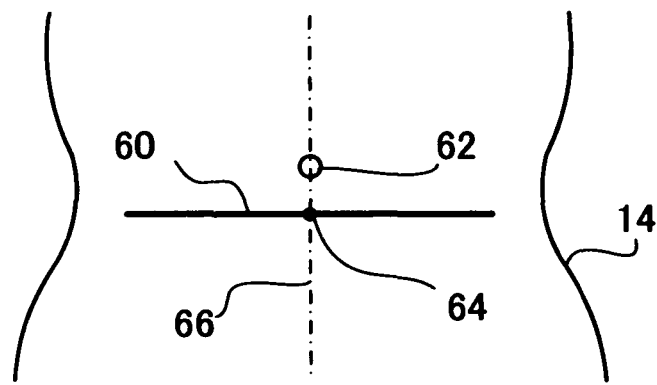
FIG. 8 is a plan view showing the abdomen of the human subject when the beams irradiate appropriate positions.

The spot light beam 62 is a projection of the center point of the connection part 20 in the longitudinal direction. Even if the linear light beam 60 irradiates the navel 64, if the spot light beam 62 does not irradiate the median plane 66, the operator can understand that the frame 16 is inclined with respect to the transverse plane orthogonal to the median plane 66. After adjusting the position of the frame 16 so that the linear light beam 60 irradiates the navel 64, the operator adjusts the orientation of the frame 16 so that the median plane 66 is irradiated with the spot light beam 62, as shown in FIG. 8. Although the median plane 66 cannot be fully identified by eye, it can be estimated by eye in a sufficient accuracy. Consequently, by this procedure, the frame 16 and thus the sensors 22a through 22h can be located in the transverse plane that passes through the navel 64 of the human subject 14 and is vertical to the median line of the human subject 14.

After adjusting the position and orientation of the frame 16 (after the decision at step S4 is affirmative), the operator manipulates the manual interface 25 for determining the abdominal width of the human subject 14 (step S5). According to the manipulation by the operator, the manual interface 25 provides the microcomputer 52 with a command to determine the abdominal width. Upon receiving the command, the microcomputer 52 causes a sensor-driving circuit (not shown) for making the light emitting elements of the sensors 22a through 22h emit light beams. Then, as described above, the microcomputer 52 estimates the abdominal width of the human subject 14 and cause the display 24 to show the abdominal width value.

Next, the operator sets the impedance measuring unit 12 on the abdomen of the human subject 14 as shown in FIG. 3 (step S6). Furthermore, by the aid of the light beams 60 and 62 from the light emitter 26, the operator adjusts the impedance measuring unit 12 to an appropriate position and an appropriate orientation with respect to the human subject 14 (steps S7 and S8).

At steps S5 and S6, irradiation by the light emitter 26 is unnecessary. Accordingly, when the operator manipulates the manual interface 25 for the width determination at step S5, the microcomputer 52 may stop driving the light emitter 26. After step S6, the operator may manipulates the manual interface 25 to drive the light emitter 26 again for emitting light onto the abdomen of the human subject 14. However, light emitter 26 may continue to emit the light at steps S5 and S6.

The target position and orientation of the impedance measuring unit 12 is such that the impedance measuring unit 12 is located without inclination in the transverse plane that passes through the navel 64 of the human subject 14 and is vertical to the median line of the human subject 14. Additionally, it is preferable that the center point 68 of the handle 34 of the impedance measuring unit 12 overlaps the navel 14 of the human subject 14, so that the electrodes 30 and 32 on an arm 36 and the electrodes 30 and 32 on the other arm 36 are generally symmetrically arranged with respect to the median plane 66.

Since the frame 16 has been already adjusted to an appropriate position and an appropriate orientation, as shown in FIG. 8, the linear light beam 60 irradiates the transverse plane that passes through the navel 64 of the human subject 14 and is vertical to the median line of the human subject 14 whereas the spot light beam 62 is positioned on the median plane 66 of the human subject 14.

Figure 9:
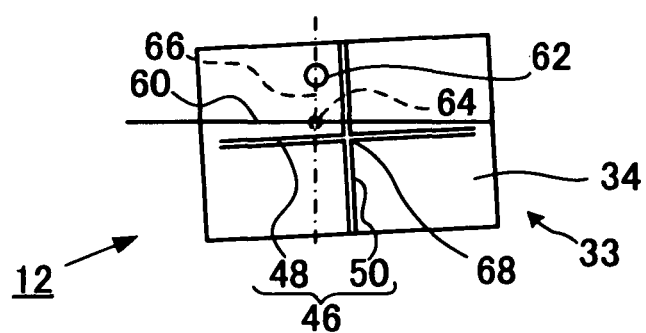
FIG. 9 is a plan view showing a handle of the impedance measuring unit when inappropriate positions of the handle are irradiated with the linear light beam and the spot light beam emitted by the light emitter in the body composition determination apparatus in FIG. 1.

By placing the impedance measuring unit 12 on the abdomen of the human subject 14, the navel 64 cannot be seen. However, by the aid of the light beams 60 and 62 and the cross-shaped mark 46, it is possible to adjust the impedance measuring unit 12 to the target position and orientation. For example, as shown in FIG. 9, if the linear light beam 60 does not irradiate the groove 48 of the mark 46 extending along the longitudinal direction of the impedance measuring unit 12, the operator can understand that the impedance measuring unit 12 is not located in the transverse plane that passes through the navel 64 of the human subject 14 and is vertical to the median line of the human subject 14. The operator adjusts the position and orientation of the impedance measuring unit 12 so that the linear light beam 60 irradiate the longitudinal groove 48, thereby locating the impedance measuring unit 12 in the transverse plane.

Figure 10:
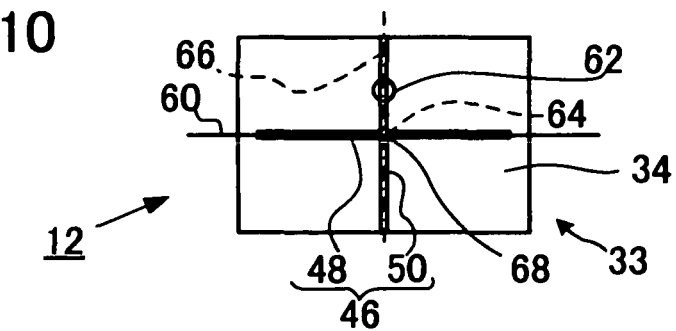
FIG. 10 is a plan view showing the handle of the impedance measuring unit when appropriate positions of the handle are irradiated with the beams.

Even if the linear light beam 60 coincides with the longitudinal groove 48, if the spot light beam 62 is not positioned on the transverse groove 50 of the mark 46, the operator can understand that the center point 68 of the handle 34 (intersection of the grooves 48 and 50) does not overlap the navel 64, and that the impedance measuring unit 12 is biased rightward or leftward relative to the human subject 14. After adjusting the position and orientation of the impedance measuring unit 12 so that the linear light beam 60 irradiates the longitudinal groove 48, the operator adjusts the position of the impedance measuring unit 12 so that the spot light beam 62 irradiate the transverse groove 50 as shown in FIG. 10. By this procedure, the impedance measuring unit 12 can be located in the transverse plane that passes through the navel 64 of the human subject 14 and is vertical to the median line of the human subject 14, whereby the electrodes 30 and 32 are also located in the transverse plane, and furthermore, the electrodes 30 and 32 on an arm 36 and the electrodes 30 and 32 on the other arm 36 can be generally symmetrically arranged with respect to the median plane 66.

After adjusting the position and orientation of the impedance measuring unit 12 (after the decision at step S8 is affirmative), the operator manipulates the manual interface 25 for measuring the bioimpedance of the abdomen of the human subject 14 (step S9). According to the manipulation by the operator, the manual interface 25 provides the microcomputer 52 with a command to measure impedance. Upon receiving the command, the microcomputer 52 drives the current-supply circuit 42 and the voltage-measurement circuit 44 to calculate the bioimpedance as described above. Furthermore, the microcomputer 52 calculates the body composition indexes and causes the display 24 to show the indexes. At step S9, irradiation by the light emitter 26 is unnecessary. Accordingly, when the operator manipulates the manual interface 25 for the impedance measurement at step S9, the microcomputer 52 stops driving the light emitter 26.

As described above, by the aid of the light beams 60 and 62 irradiated from the light emitter 26 on the human subject 14, the frame 16 is adjusted to an appropriate position and an appropriate orientation with respect to the reference position for measurement, and then the position and orientation of the electrode supporting member 33 of the impedance measuring unit 12 are adjusted so that the light beams 60 and 62 coincide with the cross mark 46 on the electrode supporting member 33 of the impedance measuring unit 12. Thus, the electrodes 30 and 32 can be accurately arranged on the reference positions for measurement accurately, so that bioimpedance can be measured with a high level of reproducibility.

Second Embodiment

Figure 11:
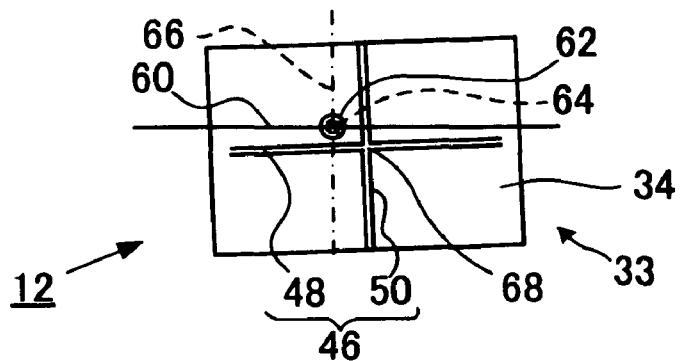
FIG. 11 is a plan view showing a handle of the impedance measuring unit when inappropriate positions of the handle are irradiated with a linear light beam and a spot light beam in a second embodiment of the present invention.
Figure 12:
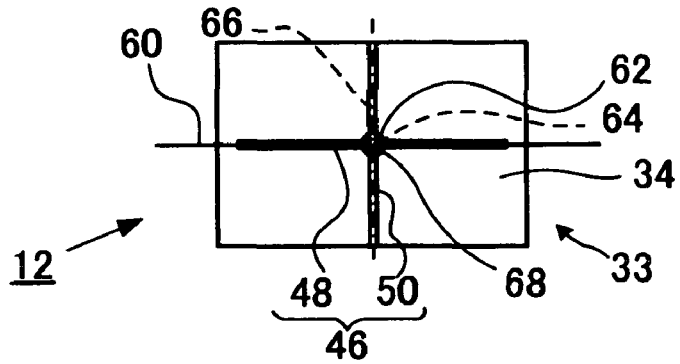
FIG. 12 is a plan view showing the handle of the impedance measuring unit when appropriate positions of the handle are irradiated with the beams in the second embodiment.

Although the spot light beam 62 irradiate a position that is apart from the line Irradiated by the linear light beam 60 in the first embodiment, the spot light beam 62 may irradiate a position on the line irradiated by the linear light beam 60 as shown in FIGS. 11 and 12. Provided that the size of the spot light beam 62 (for example, the diameter if it is circular, and the length of the side or the diagonal when it is square) is much greater than the width of the linear light beam 60, the operator can identify that there is the spot light beam 62 in addition to the linear light beam 60, with the spot light beam 62 overlapping the linear light beam 60.

Therefore, the operator can adjust the impedance measuring unit 12 from an inappropriate position (e.g., shown in FIG. 11) to an appropriate position (e.g., shown in FIG. 12) by the aid of the light beams 60 and 62 and the mark 46. Namely, matching the position of the linear light beam 60 with the longitudinal groove 48 results in positioning the impedance measuring unit 12 in the transverse plane that passes through the navel 64 of the human subject 14 and is vertical to the median line of the human subject 14, whereas matching the position of the spot light beam 62 with the transverse groove 50 results in that the electrodes 30 and 32 on an arm 36 and the electrodes 30 and 32 on the other arm 36 are generally symmetrically arranged with respect to the median plane 66. Thus, the electrodes 30 and 32 can be accurately arranged on the reference positions for measurement accurately, so that bioimpedance can be measured with a high level of reproducibility.

As in the embodiment, since the spot light beam 62 overlaps the linear light beam 60, the spot light beam 62 is almost useless for the purpose of adjusting the orientation of the frame 16 to the transverse plane orthogonal to the median plane 66 of the human subject 14. However, if the position and orientation of the frame 16 are adjusted so that the linear light beam 60 is positioned onto the navel 64 and parallel to the line between the right and left pelvises, the frame 16 can be located without inclination in the transverse plane that passes through the navel 64 of the human subject 14 and is vertical to the median line of the human subject 14.

Third Embodiment

Figure 13:
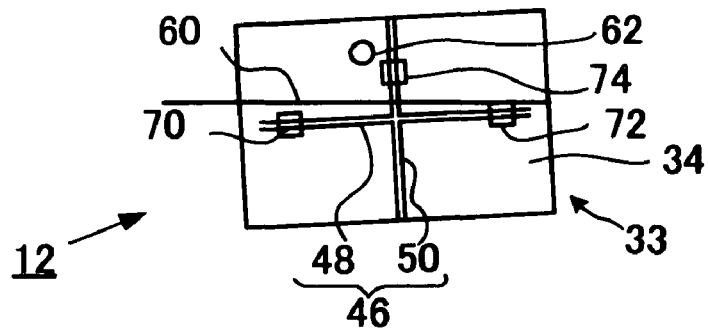
FIG. 13 is a plan view showing a handle of the impedance measuring unit when inappropriate positions of the handle are irradiated with a linear light beam and a spot light beam in a third embodiment of the present invention.
Figure 14:
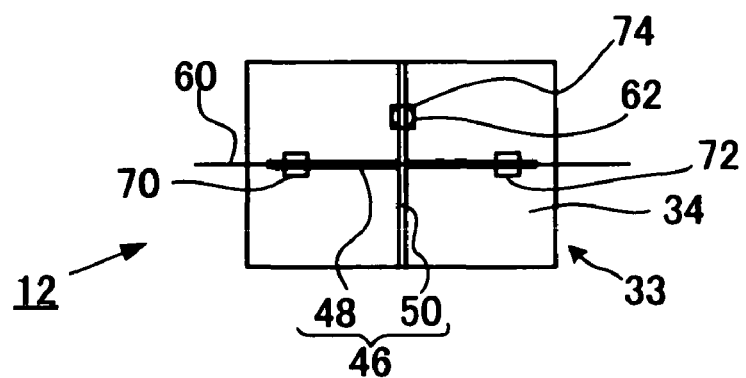
FIG. 14 is a plan view showing the handle of the impedance measuring unit when appropriate positions of the handle are irradiated with the beams in the third embodiment.

In the first embodiment, when the operator decides by eye that the light beams 60 and 62 coincide with the mark 46, the operator manipulates the manual interface 25 for measure the bioimpedance of the abdomen of the human subject 14. Instead of or in addition to the mark 46, three light receiving elements 70, 72, and 74 may be mounted on the upper surface of the handle 34 of the electrode supporting member 33 of the impedance measuring unit 12, as shown in FIGS. 13 and 14. The light receiving elements 70, 72, and 74 are, for example, but not limited to, photodiodes or CCDs (charge coupled devices).

The light receiving elements 70 and 72 aligned in a line extending along the longitudinal direction of the impedance measuring unit 12. The light receiving element 74 is apart from the line where the elements 70 and 72 lie, but is situated at the center of the handle 34 of the impedance measuring unit 12 in the longitudinal direction. The number of light receiving elements may be four or more.

In this embodiment, each of the light receiving element 70, 72, and 74 supplies a light reception signal to the microcomputer 52 (see FIG. 5) if it receives light which is stronger than a predetermined strength. In an alternative embodiment, each of the light receiving elements 70, 72, and 74 supplies a light reception signal to the microcomputer 52 if the strength of light received by the corresponding receiving element increases by an extent greater than a threshold.

When the microcomputer 52 continuously receives the light reception signals simultaneously from all light receiving elements 70, 72, and 74 for a period linger than a prescribed period, the microcomputer 52 drives the current-supply circuit 42 and the voltage-measurement circuit 44, thereby calculating the bioimpedance as described above, and then calculates the body composition indexes. In an alternative embodiment, the operator may manipulates the manual interface 25 for starting the measurement of the bioimpedance, but it is preferable that even if the operator has used the manual interface 25 for starting the measurement of the impedance, unless the microcomputer 52 continuously receives the light reception signals simultaneously from all light receiving elements 70, 72, and 74 for a period linger than a prescribed period, the microcomputer 52 does not drive the current-supply circuit 42 and the voltage-measurement circuit 44 for measuring the bioimpedance.

In the use of the third embodiment, first, by the aid of the light beams 60 and 62 from the light emitter 26 on the human subject 14, the frame 16 is adjusted to an appropriate position and orientation with respect to the reference position for measurement. Second, depending upon the light beams 60 and 62 and the light receiving element 70, 72, and 74, the impedance measuring unit 12 is adjusted from an inappropriate position (e.g., shown in FIG. 13) to an appropriate position (e.g., shown in FIG. 14). More specifically, as shown in FIG. 14, the operator adjusts the position and orientation of the impedance measuring unit 12 so that the linear light beam 60 coincides with the light receiving elements 70 and 72, and the spot light beam 62 coincides with the light receiving element 74. Matching the linear light beam 60 with the light receiving elements 70 and 72 results in that the impedance measuring unit 12 is positioned in the transverse plane that passes through the navel 64 of the human subject 14 and is vertical to the median line of the human subject 14. Matching the spot light beam 62 with the light receiving element 74 results in that the electrodes 30 and 32 on an arm 36 and the electrodes 30 and 32 on the other arm 36 are generally symmetrically arranged with respect to the median plane 66. When the electrodes 30 and 32 are thus located accurately in the reference positions for measurement, all of the light receiving elements 70, 72, and 74 supply the light reception signals to the microcomputer 52, and enable the microcomputer 52 to measure the impedance. Therefore, bioimpedance can be measured with a high level of reproducibility. As described above, the aforementioned mark 46 may be or may not be provided in this embodiment.

Fourth Embodiment

Figure 15:
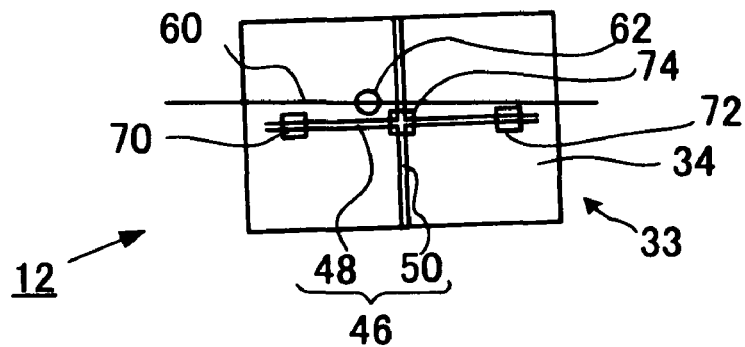
FIG. 15 is a plan view showing a handle of the impedance measuring unit when inappropriate positions of the handle are irradiated with a linear light beam and a spot light beam in a fourth embodiment of the present invention.
Figure 16:
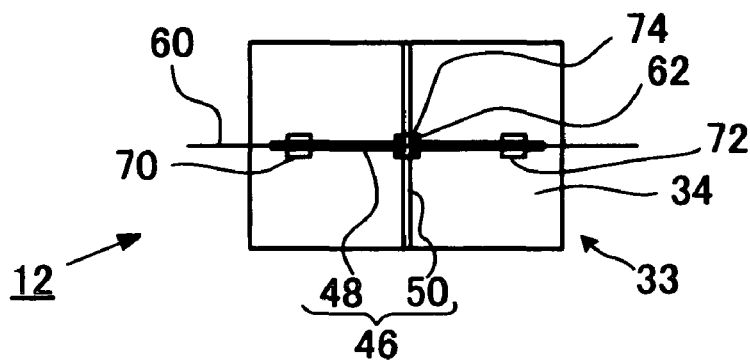
FIG. 16 is a plan view showing the handle of the impedance measuring unit when appropriate positions of the handle are irradiated with the beams in the fourth embodiment.

As similar to the third embodiment, with reference to the second embodiment, instead of or in addition to the aforementioned mark 46, three light receiving elements 70, 72, and 74 may be mounted on the upper surface of the handle 34 of the electrode supporting member 33 of the impedance measuring unit 12, as shown in FIGS. 15 and 16. In this fourth embodiment, all of the light receiving element 70, 72, and 74 are aligned in one line extending along the longitudinal direction of the impedance measuring unit 12. The light receiving element 74 is situated at the center of the handle 34 of the impedance measuring unit 12 in the longitudinal direction. The number of light receiving elements may be four or more.

Each of the light receiving element 70, 72, and 74 supplies a light reception signal to the microcomputer 52 (see FIG. 5) if it receives light which is stronger than a predetermined strength. However, the predetermined strength for the light receiving element 74 is set higher than that for the light receiving elements 70 and 72.

In an alternative embodiment, each of the light receiving elements 70, 72, and 74 supplies a light reception signal to the microcomputer 52 if the strength of light received by the corresponding receiving element increases by an extent greater than a threshold. However, the threshold for the light receiving element 74 is set higher than that for the light receiving elements 70 and 72.

In the use of the apparatus, depending on the light beams 60 and 62 and the light receiving elements 70, 72, and 74, the impedance measuring unit 12 is adjusted from an inappropriate position (e.g., shown in FIG. 15) to an appropriate position (e.g., shown in FIG. 16). More specifically, as shown in FIG. 16, the operator adjusts the position and orientation of the impedance measuring unit 12 so that the linear light beam 60 coincides with the light receiving elements 70 and 72, and the spot light beam 62 coincides with the light receiving element 74. Matching the linear light beam 60 with the light receiving elements 70 and 72 results in that the impedance measuring unit 12 is positioned in the transverse plane that passes through the navel 64 of the human subject 14 and is vertical to the median line of the human subject 14. Matching the spot light beam 62 with the light receiving element 74 results in that the electrodes 30 and 32 on an arm 36 and the electrodes 30 and 32 on the other arm 36 are generally symmetrically arranged with respect to the median plane 66. When the electrodes 30 and 32 are thus located accurately in the reference positions for measurement, all of the light receiving elements 70, 72, and 74 supply the light reception signals to the microcomputer 52, and enable the microcomputer 52 to measure the impedance. Therefore, bioimpedance can be measured with a high level of reproducibility. The aforementioned mark 46 may be or may not be provided in this embodiment.

As described above, the sensitivity of the light receiving element 74 is lower than that of the light receiving elements 70 and 72, so that the light receiving element 74 does not output the light reception signal if only the linear light beam 60 coincides with the light receiving element 74. When the light receiving element 74 is irradiated by the spot light beam 62 in addition to by the linear light beam 60, the light receiving element 74 outputs the light reception signal.

Fifth Embodiment

Figure 17:
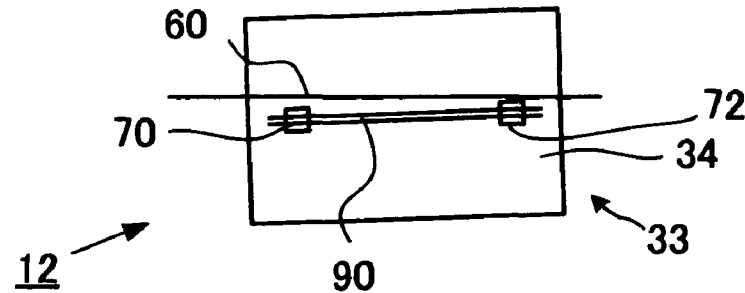
FIG. 17 is a plan view showing a handle of the impedance measuring unit when an inappropriate position of the handle is irradiated with a linear light beam in a fifth embodiment of the present invention.
Figure 18:
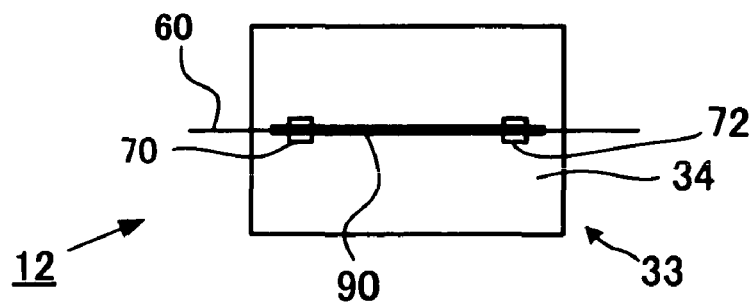
FIG. 18 is a plan view showing the handle of the impedance measuring unit when an appropriate position of the handle is irradiated with the beam in the fifth embodiment.

In the above-described embodiments, the light emitter 26 emits the linear light beam 60 and the spot light beam 62. However, as shown in FIGS. 17 and 18, the light emitter 26 may emit only a single linear light beam 60. In such an embodiment, when light receiving elements are used, only two light receiving elements 70 and 72 may be used, which extend along the longitudinal direction of the electrode supporting member 33 of the impedance measuring unit 12. In such an embodiment, when a mark is used, the mark is not necessary to be cross, and instead, a linear mark 90 may be used, which extends along the longitudinal direction of the electrode supporting member 33 of the impedance measuring unit 12. As the mark 90, a line which is printed or handwritten, a raised line, or a linear groove may used. In FIGS. 17 and 18, the light receiving elements 70 and 72 and the mark 90 are illustrated. However, it is possible that to provide only the light receiving elements 70 and 72 or to provide only the mark 90.

In the use of the apparatus, depending on the linear light beam 60 and the linear mark 90 (and/or two light receiving elements 70 and 72), the impedance measuring unit 12 is adjusted from an inappropriate position (e.g., shown in FIG. 17) to an appropriate position (e.g., shown in FIG. 18). More specifically, as shown in FIG. 18, the operator adjusts the position and orientation of the impedance measuring unit 12 so that the linear light beam 60 coincides with the mark 90 (and/or the light receiving elements 70 and 72). Matching the linear light beam 60 with the linear mark 90 (and/or the light receiving elements 70 and 72) results in that the impedance measuring unit 12 is positioned in the transverse plane that passes through the navel 64 of the human subject 14 and is vertical to the median line of the human subject 14.

Sixth Embodiment

Figure 19:
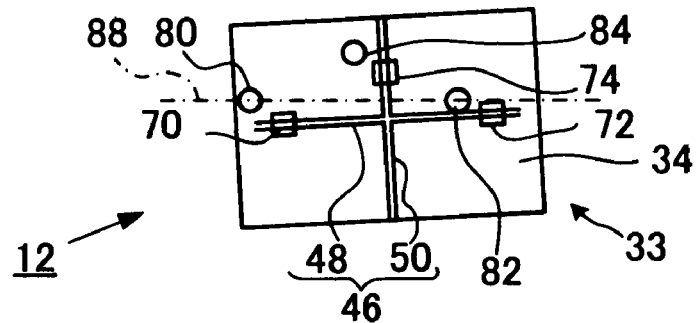
FIG. 19 is a plan view showing a handle of the impedance measuring unit when inappropriate positions of the handle are irradiated with three spot light beam in a sixth embodiment of the present invention.
Figure 20:
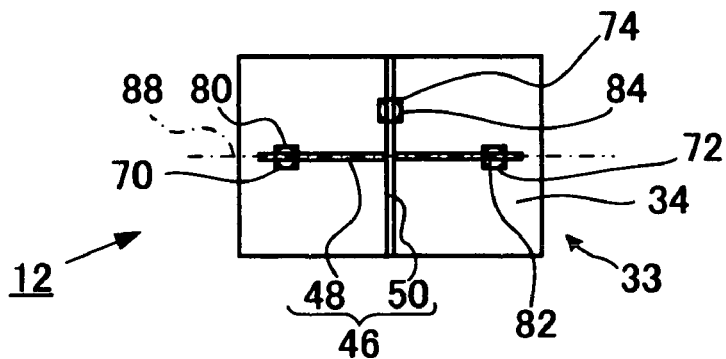
FIG. 20 is a plan view showing the handle of the impedance measuring unit when appropriate positions of the handle are irradiated with the beams in the sixth embodiment.

As shown in FIGS. 19 and 20, the light emitter 26 may emits three spot light beams 80, 82, and 84. The light beams 80 and 82 irradiate respectively in their radiation fields two spot areas on a straight line 88 extending parallel to the longitudinal direction of the connection part 20 of the frame 16. Consequently, the phantom line 88 passing through the spot light beams 80 and 82 is a projection of the longitudinal axis of the connection part 20. The light beam 84 is emitted from the center point of the connection part 20 in the longitudinal direction toward the direction vertical to the connection part 20, and irradiates a spot area in its radiation field. Consequently, the spot light beam 84 is a projection of the center point of the connection part 20 in the longitudinal direction.

In the use of the apparatus, depending on the spot light beam 80, 82, and 84 and the mark 46 (and/or light receiving element 70, 72, and 74), the impedance measuring unit 12 is adjusted from an inappropriate position (e.g., shown in FIG. 19) to an appropriate position (e.g., shown in FIG. 20). More specifically, as shown in FIG. 20, the operator adjusts the position and orientation of the impedance measuring unit 12 so that the spot light beams 80 and 82 coincide with the longitudinal groove 48 of the mark 46 (and/or the light receiving elements 70 and 72), and the other spot light beam 84 coincides with the transverse groove 50 of the mark 46 (and/or the light receiving element 74). Matching the spot light beams 80 and 82 with the longitudinal groove 48 (and/or the light receiving elements 70 and 72) results in that the impedance measuring unit 12 is positioned in the transverse plane that passes through the navel 64 of the human subject 14 and is vertical to the median line of the human subject 14. Matching the other spot light beam 84 with the transverse groove 50 (and/or the light receiving element 74) results in that the electrodes 30 and 32 on an arm 36 and the electrodes 30 and 32 on the other arm 36 are generally symmetrically arranged with respect to the median plane 66.

Seventh Embodiment

Figure 21:
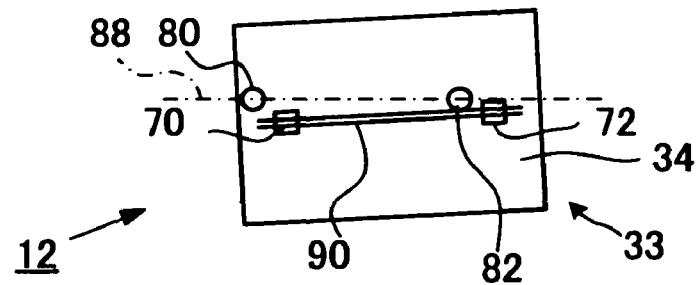
FIG. 21 is a plan view showing a handle of the impedance measuring unit when inappropriate positions of the handle are irradiated with three spot light beam in a seventh embodiment of the present invention.
Figure 22:
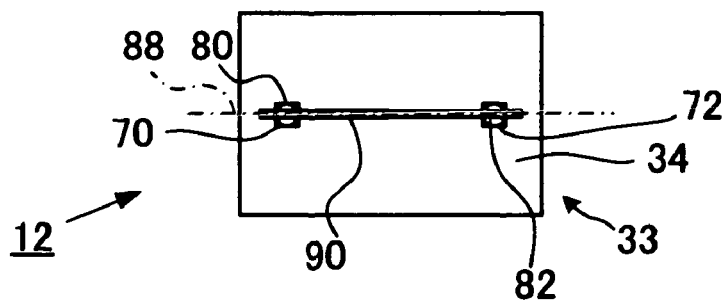
FIG. 22 is a plan view showing the handle of the impedance measuring unit when appropriate positions of the handle are irradiated with the beams in the seventh embodiment.

As shown in FIGS. 21 and 22, the light emitter 26 may emit only two spot light beams 80 and 82. In such an embodiment, when light receiving elements are used, only two light receiving elements 70 and 72 may be used, which extend along the longitudinal direction of the electrode supporting member 33 of the impedance measuring unit 12. In such an embodiment, when a mark is used, the mark is not necessary to be cross, and instead, a linear mark 90 may be used, which extends along the longitudinal direction of the electrode supporting member 33 of the impedance measuring unit 12. As the mark 90, a line which is printed or handwritten, a raised line, or a linear groove may used. In FIGS. 17 and 18, the light receiving elements 70 and 72 and the mark 90 are illustrated. However, it is possible that to provide only the light receiving elements 70 and 72 or to provide only the mark 90.

In the use of the apparatus, depending on the spot light beams 80 and 82 and the linear mark 90 (and/or two light receiving elements 70 and 72), the impedance measuring unit 12 is adjusted from an inappropriate position (e.g., shown in FIG. 21) to an appropriate position (e.g., shown in FIG. 22). More specifically, as shown in FIG. 22, the operator adjusts the position and orientation of the impedance measuring unit 12 so that the spot light beams 80 and 82 coincide with the mark 90 (and/or the light receiving elements 70 and 72). Matching the spot light beams 80 and 82 with the linear mark 90 results in that the impedance measuring unit 12 is positioned in the transverse plane that passes through the navel 64 of the human subject 14 and is vertical to the median line of the human subject 14.

The use of the light receiving elements 70 and 72 leads to more precise positioning than can be obtained by the use of only the linear mark 90. Matching two spot light beams 80 and 82 with two light receiving elements 70 and 72 results in that impedance measuring unit 12 is positioned in the transverse plane that passes through the navel 64 of the human subject 14 and is vertical to the median line of the human subject 14 and in that the electrodes 30 and 32 on an arm 36 and the electrodes 30 and 32 on the other arm 36 are generally symmetrically arranged with respect to the median plane 66.

Other Modifications

In the above-described embodiments, a plurality of sensors 22 are fixed to the frame 16. However, it is possible that a sensor is attached movably to each of legs 18 and 18b, and each sensor is driven at known positions for measuring distances from the corresponding sensor to a plurality of measured points on the outline of the human subject.

In the above-described embodiments, optical distance sensors 22 are used as distance measuring devices for measuring distances from a plurality of known positions to a plurality of measured points on the outline of the human subject 14 in a noncontact manner. However, distance measuring devices may be other types of noncontact distance measuring devices.

In the above-described embodiments, body composition indexes are calculated directly from the abdominal width and the bioimpedance of the human subject 14. However, it is possible that another index (for example, the cross-sectional area of the abdomen or the waist circumference) is calculated from the abdominal width, and then the body composition indexes are calculated from such an index and the bioimpedance.

In the above-described embodiments, for determining the abdominal width, the sensors 22a through 22h are deployed in the transverse plane that passes through the navel of the human subject 14 and is vertical to the median line of the human subject 14. However, by adjusting the location of the light emitter 26 relative to the sensors 22a through 22h, the sensors 22a through 22h may be deployed in another transverse plane vertical to the median line of the human subject 14 for determining the abdominal width.

In the above-described embodiments, for measuring the bioimpedance of the abdomen, the electrodes 30 and 32 are also deployed in the transverse plane that passes through the navel of the human subject 14 and is vertical to the median line of the human subject 14. However, by adjusting the location of the mark (and/or the light receiving elements) on the handle 34 relative to the electrodes 30 and 32, the electrodes 30 and 32 may be deployed in another transverse plane vertical to the median line of the human subject 14 for measuring the bioimpedance of the abdomen.

What is claimed is:

1. An abdominal impedance measurement apparatus comprising:
    a plurality of electrodes for measuring an abdominal impedance of a human subject and configured for placement against an abdomen of said human subject;
    an electrode supporting member for supporting the electrodes;
    a frame positionable around the abdomen of the human subject;
    a light emitter supported by the frame for emitting light beams toward the inside of the frame onto at least two points; and
    a mark provided at the electrode supporting member, comprising a part extending along a longitudinal direction of the electrode supporting member, wherein the light beams are emitted towards the abdomen and toward the electrode supporting member and the mark being capable of being irradiated with the light beams to allow positioning of the electrodes.

2. The abdominal impedance measurement apparatus of claim 1, wherein the electrodes are aligned along the longitudinal direction of the electrode supporting member.

3. The abdominal impedance measurement apparatus of claim 1, wherein the electrodes are aligned along the longitudinal direction of the electrode supporting member, the light emitter emitting light beams onto at least three points, the mark being of a cross-shape comprising a part extending along the longitudinal direction of the electrode supporting member and another part orthogonal to the part extending along the longitudinal direction.

4. The abdominal impedance measurement apparatus of claim 3, wherein the light emitter emits the light beams onto a straight line and a spot.

5. An abdominal impedance measurement apparatus comprising:
    a plurality of electrodes for measuring an abdominal impedance of a human subject and configured for placement against an abdomen of said human subject;
    an electrode supporting member for supporting the electrodes;
    a frame positionable around the abdomen of the human subject;
    a light emitter supported by the frame for emitting light beams toward the inside of the frame onto at least two points; and
    at least two light receiving elements provided at the electrode supporting member, the light receiving elements being capable of being irradiated with the at least two points of the light beams, the light receiving elements being aligned in a line extending along a longitudinal direction of the electrode supporting member, wherein the light beams are emitted towards the abdomen and toward the electrode supporting member and each of the light receiving elements outputting a light reception signal when the light receiving element receives the light beam which is stronger than a predetermined threshold.

6. The abdominal impedance measurement apparatus of claim 5, wherein the electrodes are aligned along a longitudinal direction of the electrode supporting member.

7. The abdominal impedance measurement apparatus of claim 5, wherein the electrodes are aligned along the longitudinal direction of the electrode supporting member, the light emitter emitting light beams onto at least three points, at least three light receiving elements being provided at the electrode supporting member, the light receiving elements being capable of being irradiated with the at least three points of the light beams, two of the light receiving elements being aligned in a line extending along the longitudinal direction of the electrode supporting member.

8. The abdominal impedance measurement apparatus of claim 7, wherein the light emitter emits the light beams onto a straight line and a spot.

9. A body composition determination apparatus comprising:
    the abdominal impedance measurement apparatus of claim 1;
    distance measuring devices located at the frame, each of the distance measuring devices outputting a signal corresponding to a distance from the distance measuring device to an abdominal part of the human subject;
    a width estimator for estimating a width value of the abdominal part of the human subject on the basis of signals output by the distance measuring devices; and
    a body composition index calculator for calculating an index of a body composition of the human subject on the basis of the impedance measured by the abdominal impedance measurement apparatus and the width value estimated by the width estimator.

10. A body composition determination apparatus comprising:
    the abdominal impedance measurement apparatus of claim 5;
    distance measuring devices located at the frame, each of the distance measuring devices outputting a signal corresponding to a distance from the distance measuring device to an abdominal part of the human subject;
    a width estimator for estimating a width value of the abdominal part of the human subject on the basis of signals output by the distance measuring devices; and
    a body composition index calculator for calculating an index of a body composition of the human subject on the basis of the impedance measured by the abdominal impedance measurement apparatus and the width value estimated by the width estimator.

* * * * *